United States Patent [19]
Cavazza

[11] Patent Number: 5,883,127
[45] Date of Patent: Mar. 16, 1999

[54] USE OF LOWER ALKANOYL L-CARNITINES TO PRODUCE A MEDICAMENT SUITABLE FOR THE THERAPEUTIC TREATMENT OF RETINOPATHIES

[75] Inventor: Claudio Cavazza, Rome, Italy

[73] Assignee: Sigma-Tau Industrie Farmaceutiche Riunite S.p.A, Rome, Italy

[21] Appl. No.: 969,939

[22] Filed: Nov. 25, 1997

[30] Foreign Application Priority Data

Dec. 3, 1996 [IT] Italy ................................ RM96A0827

[51] Int. Cl.$^6$ .................................................. A61K 31/205
[52] U.S. Cl. ............................................ 514/556; 514/912
[58] Field of Search ...................... 514/556, 912

[56] References Cited

PUBLICATIONS

WPIDS Abstract 97–01672 (1996). Horrobin et al.

*Primary Examiner*—Zohreh Fay
*Attorney, Agent, or Firm*—Oblon, Spivak, McClelland, Maier & Neustadt, P.C.

[57] ABSTRACT

The use of lower alkanoyl L-carnitines (e.g. acetyl L-carnitine) and the pharmacologically acceptable salts thereof to produce a medicament suitable for the therapeutic treatment of retinopathies, e.g. the age-related maculopathy (ARM) and non-age-related maculopathy (nARM), is disclosed.

17 Claims, No Drawings

USE OF LOWER ALKANOYL L-CARNITINES TO PRODUCE A MEDICAMENT SUITABLE FOR THE THERAPEUTIC TREATMENT OF RETINOPATHIES

The present invention relates to the use of lower alkanoyl L-carnitines and the pharmacologically acceptable salts thereof to produce a medicament suitable for the therapeutic treatment of retinopathies, particularly the age-related maculopathy (ARM) and non-age-related maculopathy (nARM) and for the prophylaxis and treatment of age-related macular degeneration (AMD). Further retinopathies that can be successfully treated according to the present invention include diabetic retinopathy, neuroretinopathies, e.g. the Batten-Mayou disease and the inherited dominant drusen.

By "lower" alkanoyl, any alkanoyl group having 2–6 carbon atoms is meant. Acetyl, propionyl, valeryl and isovaleryl are preferred alkanoyl groups. Acetyl is particularly preferred.

Previous ophthalmological applications of both acetyl L-carnitine and acetyl D-carnitine are already known.

U.S. Pat. No. 5,037,851 describes the use of acetyl L-carnitine and its pharmacologically acceptable salts in the therapeutic treatment of cataract.

U.S. Pat. Nos. 5,145,871 and 5,432,199 describe the use of acetyl D-carnitine and its pharmacologically acceptable salts in the therapeutic treatment of glaucoma.

There is no relationship between the above-mentioned diseases and age-related macular degeneration other than the self-evident fact, of no aetiological or therapeutic importance, that these are all diseases of the eye.

Cataract is the disease consisting in congenital or degenerative progressive opacification of the lens, i.e. of the biconvex, transparent lenticular structure of the eye located between the iris and the vitreous body.

Although the risk factors for cataract and, particularly, for AMD have not been clearly defined, it has been demonstrated that surgical removal of a cataract leads to progressive aggravation of any associated maculopathy (Liu et al., Am. J. Public Health 1989; 79: 765–769; Van der Schaft T. et al., Br. J. Ophthalmology 1994; 78: 441–445; Klein R. et al., Arch. Ophthalmol. 1994; 112: 191–196; Pollack A. et al., Ophthalmology 1996; 103: 1546–1554).

The term glaucoma refers to a group of eye diseases characterised by a progressive degeneration of optic nerve due to either vascular or mechanical pathogenesis, this latter consisting of an increased resistance to the outflow of aqueous humour via the trabecular reticulum at the level of the irido-corneal junction.

Age-related macular degeneration, on the other hand, is a disease belonging to the retinopathy group and specifically involving degeneration of the macula, one of the structures of the retina.

The macula is a yellowish ovoid zone measuring 2–5 mm in diameter located on the surface of the retina in line with the centre of the cornea. This zone is densely packed with highly specialised photoreceptors, particularly cones, for the perception of light and is therefore regarded as the site of maximum acute and discriminatory visual capacity.

Degeneration of this area of the retina, as occurring in age-related macular degeneration (AMD), is an important cause of reduction and even of loss of vision in the elderly, particularly in industrialised Western countries and is therefore a disease with a substantial social and economic impact.

A recent epidemiological study (Br. J. Ophthalmol. 1996; 80: 9–14) has revealed, for instance, that in Great Britain alone 35,000 people are registered every year as totally or partially blind, and that more than 50% of these suffer from AMD. According to the Framingham Study (Surv. Ophthalmol. 1980; 24 (suppl.): 355–610), age-related macular degeneration may affect 20% of the population aged 65 and above as compared to less than 2% of the population aged from 52 to 64. The Beaver Dam Eye Study (Ophthalmology, 1992; 99: 933–943) has shown that approximately 35% of the population aged 75 and over are suffering from AMD.

This means that from 6 to 11% of the elderly population in the United States today are progressively limited in their social life as their vision deteriorates.

A European study (Acta Ophthalmologica Scandinavica, 1995, suppl. 217) reports an increase in the prevalence of age-related macular abnormalities from 14.6% in the 60- to 64-year-old age group to 45% in the 75- to 80-year-old age group.

The aetiology of the disease has yet to be thoroughly clarified, amongst other things because the studies on the causes of AMD have been limited by a shortage of suitable tissues from human donors and by the lack of a representative animal model.

The term AMD encompasses a broad range of morphological abnormalities which reflect the complexity of a disease which is probably of multifactorial aetiology with a complex interaction between genetic predisposition, ageing, environmental factors and life-style.

The disease is of a progressive nature.

ARM is a disease of the macular area of the retina which is mostly detected clinically after the age of 50 and is characterised by one or more of the following signs:

presence of discontinuous yellowish-white excrescences or nodules (spots) called drusen which are external to the neuroretina or the retinal pigment epithelium. They may be soft and confluent (soft drusen), often with indistinct margins. Hard drusen, which are usually present in both retinas affected and not affected by ARM, are not in themselves signs of the disease;

areas of increased pigmentation or hyperpigmentation associated with the drusen;

areas of depigmentation or hypopigmentation of the retinal pigment epithelium without visible choroidal vessels associated with the drusen. The last stage of ARM is called age-related macular degeneration (AMD). AMD thus constitutes the ultimate evolution of ARM and includes both dry or atrophic AMD and wet or exudative AMD.

For a more detailed definition and international classification of ARM and AMD, see Survey of Ophthalmology 1995; 39: 367–374, a publication which is incorporated herein by reference.

To date, there is no valid therapy either for slowing down the aggravation of the macular degeneration or for reducing the high incidence of blindness as a complication of AMD, with the exception of parasurgery by laser photocoagulation in forms of neovascularisation of the choroid (i.e. of the membrane enveloping the retina) which are, however, the less frequent forms of degeneration. Therapeutic measures in ARM and AMD are currently limited, in practice, to alimentary supplementation for prophylactic purposes with vitamins, mineral salts and antioxidants. These treatments, however, present no proven efficacy. Particularly serious, moreover, is the fact that the macular degeneration is very often bilateral.

It will be appreciated, therefore, that there is a need for a medicament capable of slowing down and possibly arresting the progress of ARM, nARM and AMD.

The object of the present invention is therefore to provide such a medicament.

It has now been found that the aforesaid alkanoyl L-carnitines and particularly acetyl L-carnitine and its pharmacologically acceptable salts achieve the following objectives: therapy of age-related maculopathy (ARM), therapy of age-related macular degeneration (AMD) both in the dry and exudative forms, pharmacological therapy combined with surgery (laser photocoagulation for exudative forms of AMD), support therapy in ARM patients submitted to surgery for cataract in order to prevent ARM from developing into AMD, and therapy for non-age-related maculopathy (nARM) in patients aged under 50.

The object of the present invention is therefore the use of an alkanoyl L-carnitine (the term "alkanoyl" being as previously defined) or the pharmacologically acceptable salts thereof to produce a medicament suitable for the therapeutic treatment of age-related maculopathy (ARM) and non-age-related maculopathy (nARM) and for the prophylaxis and treatment of age-related macular degeneration (AMD), as well as for the treatment of the other retinopathies previously indicated.

It has also been found that, although the daily dose to be administered depends, according to the judgement of the primary care physician, on the subject's weight, age and general condition, it is generally advisable to administer from 1 to 4 g/day, and preferably 2 to 3 g/day of acetyl L-carnitine or an equimolar amount of one of the other aforesaid alkanoyl L-carnitines or a pharmacologically acceptable salts thereof, even if larger doses can be administered in view of the substantial non-toxicity of acetyl L-carnitine and the other alkanoyl L-carnitines.

The medicament of the invention can be obtained by mixing the active ingredient (acetyl L-carnitine or one of the other alkanoyl L-carnitines or a pharmaceutically acceptable salts thereof) with appropriate excipients suitable for the formulation of compositions which lend themselves to enteral administration (particularly oral) or to parenteral administration (particularly intramuscular or intravenous). All such excipients are well known to experts in pharmacy and pharmaceutical technology.

What is meant by pharmacologically acceptable salts of an alkanoyl L-carnitine are any of its salts with an acid that do not give rise to unwanted side effects. Such acids are well known to pharmacologists and to experts in pharmacy and pharmaceutical technology.

Non limiting examples of such salts are chloride, bromide, orotate, acid aspartate, citric acid, acid phosphate, fumarate and acid fumarate, lactate, maleate and acid maleate, acid oxalate, acid sulphate, glucose phosphate, tartrate and acid tartrate.

A number of examples of formulations in the form of unitary doses are provided here below.

(a) Formulation for tablets
One tablet contains:
Active ingredient
acetyl L-carnitine.HCl 590 mg
(corresponding to 500 mg of acetyl L-carnitine, inner salt)
Excipients
microcrystalline cellulose, polyvinylpyrrolidone, magnesium stearate, cellulose acetate phthalate, diethylphthalate, dimethicone
(b) Formulation for intravenous injectable ampoules
One ampoule contains:
Active ingredient
acetyl L-carnitine 500 mg
Excipients
mannitol
One solvent ampoule contains:
water for injections, q.s. up to 5 ml
(c) Formulation for sachets
One sachet contains:
Active ingredient
acetyl L-carnitine.HCl 590 mg
(corresponding to 500 mg of acetyl L-carnitine, inner salt)
Excipients
silica gel, sodium saccharine, hydroxypropyl-cellulose, sodium bicarbonate, tonic water (1×1000), mannitol.
(d) Formulation for extemporaneous solution
One 12.316 g vial contains:
Active ingredient
acetyl L-carnitine.HCl 12.0 g (corresponding to 10.17 g base)
Excipients
methyl p-hydroxybenzoate, propyl p-hydroxybenzoate, polyvinylpyrrolidone.

Whilst several clinical studies have been conducted, the results of a study wherein acetyl L-carnitine was used as active ingredient is summarised hereinbelow:

Fifteen patients aged from 40 to 85 years suffering from age-related maculopathy with drusen-type macular lesions were treated for 3 to 6 months with 2 g of acetyl L-carnitine daily per os.

At the end of the acetyl L-carnitine treatment, the following findings were detected:

ocular fundus unchanged;

no increase in number or development of drusen at fluorangiography;

no deterioration of photopic visual acuity;

no deterioration of contrast sensitivity;

no deterioration of computerised threshold campimetry;

no deterioration of electrofunctional test variables such as: visual evoked potentials, patterns at low, medium and high spatial frequencies; flash-type visual potentials; photopic, scotopic and massive electroretinogram (ERG); threshold electro-retinogram (STR); oscillatory potentials.

Several patients also showed a marked improvement in a number of electrofunctional tests such as STR and massive ERG, and in the photopic visual acuity tests.

Absorption of the exudate associated with the drusen was also observed.

I claim:

1. A method for therapeutic treatment of a retinopathy comprising administering to a patient in need thereof an effective therapeutic amount of a medicament comprising an alkanoyl L-carnitine, wherein the alkanoyl group has 2–6 carbon atoms, or a pharmacologically acceptable salt thereof.

2. The method of claim 1, wherein the alkanoyl L-carnitine is selected from the group consisting of acetyl, propionyl, valeryl and isovaleryl L-carnitine.

3. The method of claim 1, wherein the alkanoyl L-carnitine is acetyl L-carnitine.

4. The method of claim 1, wherein the retinopathy is selected from the group consisting of age-related maculopathy (ARM), non-age-related maculopathy (nARM), diabetic retinopathy, neuro-retinopathies and age-related macular degeneration (AMD).

5. The method of claim 2, wherein the retinopathy is selected from the group consisting of age-related maculopathy (ARM), non-age-related maculopathy (nARM), diabetic retinopathy, neuro-retinopathies and age-related macular degeneration (AMD).

6. The method of claim 3, wherein the retinopathy is selected from the group consisting of age-related maculopathy (ARM), non-age-related maculopathy (nARM), diabetic retinopathy, neuro-retinopathies and age-related macular degeneration (AMD).

7. The method of claim 1, wherein said treatment is by oral or parenteral administration.

8. The method of claim 2, wherein said treatment is by oral or parenteral administration.

9. The method of claim 3, wherein said treatment is by oral or parenteral administration.

10. The method of claim 7, wherein said administration is 1–4 g/day.

11. The method of claim 10, wherein said administration is 2–g/day.

12. The method of claim 1, wherein the pharnacologically acceptable salt is selected from the group consisting of chloride, bromide, orotate, acid aspartate, citric acid, acid phosphate, fumarate, acid fumarate, lactate, maleate, acid maleate, acid oxalate, acid sulphate, glucose phosphate, tartrate, and acid tartrate.

13. The method of claim 2, wherein the pharmacologically acceptable salt is selected from the group consisting of chloride, bromide, orotate, acid aspartate, citric acid, acid phosphate, fumarate, acid fumarate, lactate, maleate, acid maleate, acid oxalate, acid sulphate, glucose phosphate, tartrate, and acid tartrate.

14. The method of claim 3, wherein the pharmacologically acceptable salt is selected from the group consisting of chloride, bromide, orotate, acid aspartate, citric acid, acid phosphate, fumarate, acid fumarate, lactate, maleate, acid maleate, acid oxalate, acid sulphate, glucose phosphate, tartrate, and acid tartrate.

15. The method of claim 4, wherein the neuro-retinopathy is selected from the group consisting of Batten-Mayou disease and inherited dominant drusen.

16. The method of claim 5, wherein the neuro-retinopathy is selected from the group consisting of Batten-Mayou disease and inherited dominant drusen.

17. The method of claim 6, wherein the neuro-retinopathy is selected from the group consisting of Batten-Mayou disease and inherited dominant drusen.

* * * * *